(12) United States Patent
Wildes et al.

(10) Patent No.: US 6,323,661 B1
(45) Date of Patent: Nov. 27, 2001

(54) MEASUREMENT OF PRINTED CIRCUIT-TO-CONDUCTIVE SUBSTRATE CONTACT RESISTANCE

(75) Inventors: Douglas Glenn Wildes, Ballston Lake; George Charles Sogoian, Glenville, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/562,151

(22) Filed: May 1, 2000

Related U.S. Application Data

(60) Provisional application No. 60/132,195, filed on May 3, 1999.

(51) Int. Cl.[7] .......................... G01N 27/04; G01R 27/08; G01R 31/26
(52) U.S. Cl. ............................................. 324/719; 324/715
(58) Field of Search .................................. 324/693, 713, 324/715, 718, 719

(56) References Cited

U.S. PATENT DOCUMENTS

| | | | |
|---|---|---|---|
| 4,218,650 | * | 8/1980 | Matzen .................................. 324/719 |
| 4,404,489 | | 9/1983 | Larson, III et al. .................. 310/334 |
| 4,672,314 | * | 6/1987 | Kokkas ................................. 324/765 |
| 5,202,641 | * | 4/1993 | Unvala ................................. 324/715 |
| 5,396,184 | * | 3/1995 | Frank et al. ......................... 324/713 |
| 5,450,016 | * | 9/1995 | Masumori ............................ 324/713 |
| 5,585,734 | * | 12/1996 | Meuris et al. ....................... 324/719 |
| 5,663,651 | * | 9/1997 | Hada .................................... 324/713 |
| 5,691,648 | * | 11/1997 | Cheng .................................. 324/715 |

* cited by examiner

Primary Examiner—Glenn W. Brown
(74) Attorney, Agent, or Firm—Jill M. Breedlove; Christian Cabou

(57) ABSTRACT

To determine electrical resistance of an ohmic contact between a flexible printed circuit and a metallized layer upon a substrate of piezoelectric material, the printed circuit is provided with two exposed metal pads, in close proximity to each other, and two electrical leads from each pad to locations on the printed circuit that are accessible for probing with a four-lead resistance meter. For measurement of contact resistance in process development and process capability studies, many sets of such pads, of a variety of sizes, may be combined into a single printed circuit. For in-process monitoring of transducer manufacturing, a small number of contact resistance measurement pads may be designed into production printed circuits.

3 Claims, 7 Drawing Sheets

MEASUREMENT OF PRINTED CIRCUIT-TO-CONDUCTIVE SUBSTRATE CONTACT RESISTANCE

RELATED PATENT APPLICATION

This application claims the benefit of priority from U.S. Provisional Application Ser. No. 60/132,195 filed on May 3, 1999.

GOVERNMENT RIGHTS

The U.S. Government may have certain rights in this invention pursuant to contract number N00014-96-C0189 awarded by the U.S. Department of the Navy.

FIELD OF THE INVENTION

This invention relates to methods and devices for measuring contact resistance between conductive surfaces in electrical devices and, more particularly, to measuring contact resistance between a metallized surface of a printed circuit and a contacting conductive surface, e.g., a metallized surface of a phased-array ultrasound transducer for use in a diagnostic medical imaging system.

BACKGROUND OF THE INVENTION

Most modern transducers for use in diagnostic medical ultrasound imaging are phased arrays, made up of single or multiple rows of electrically and mechanically independent transducer elements. Each transducer element is a layered structure comprising an acoustic absorber, a piezoelectric ceramic (hereinafter "piezoceramic") layer, one or more acoustic matching layers, and a front wear plate or focusing lens. Typically, one or more flexible printed circuits (hereinafter "flex circuits") are used to make electrical connections (signal and ground) from the piezoceramic layer to the signal processing electronics, or to a bundle of coaxial cables which ultimately connect to the signal processing electronics. One known method of connecting the flex circuit to the piezoceramic uses ohmic contacts; i.e., exposed metal pads on the flex circuit are laminated, using high pressure and a thin layer of non-conductive epoxy, to the electroded surface of the piezoceramic layer. If the flex circuit and piezoceramic surfaces are microscopically rough and the epoxy layer is sufficiently thin, then an electrical connection is achieved via a distribution of direct contacts between high points on the piezoceramic surface and high points on the flex circuit.

The quality of such an ohmic electrical connection is very sensitive to material and process parameters that can be difficult to control (such as surface roughness, flatness, and parallelism; epoxy viscosity; lamination pressure). The resistances of both good and bad contacts are small compared to other impedances in the circuit for a transducer element, so that it is next to impossible to non-destructively measure the quality of the electrical connection. Typical measurements of transducer performance, such as low-frequency capacitance measurements or high-frequency impulse response measurements, can detect open or severely degraded ohmic contacts but cannot discriminate between good contacts and weak contacts which may degrade and become unreliable over time. If contact problems are suspected, either the back or front layers of the transducer must be removed to obtain access to the flex circuit-to-ceramic bond area. The ceramic electrode and the flex circuit metallization are separately exposed and connected to the leads of a resistance meter. This method of analysis is both destructive and laborious.

SUMMARY OF THE INVENTION

In accordance with a preferred embodiment of the invention, electrical resistance of an ohmic contact between two conductive substrates, e.g., a flexible printed circuit and a metallized substrate made of piezoelectric ceramic material, may be measured by employing two metal pads on the surface of the flex circuit, separated from each other but in close proximity thereto. Two electrical leads extend from each flex pad to locations on the flex circuit that are accessible for probing with a four-lead resistance meter (e.g., a milliohmmeter) and may be remote from the flex circuit-to-substrate ohmic connection. For laboratory measurement of contact resistance, many sets of such pads, of a variety of sizes, may be combined into a single flex circuit.

In accordance with a further aspect of the invention, for in-process monitoring of transducer manufacturing, a small number of contact resistance measurement pads may be designed into production flex circuits. If bad electrical contacts can be detected, then bad parts can be scrapped early in the production line. If process drift can be monitored in production, then lamination problems can be corrected before many transducers are affected. For in-process monitoring, the contact resistance measurement circuit must be arranged in a way which does not interfere with either the normal fabrication processes or the optimal design and operation of the transducer. Preferably, the contact resistance measurement circuit and method should add negligible cost to the transducer components and fabrication processes.

The invention is described in the context of, but is not limited in applicability to, the manufacturing of phased-array ultrasound transducers. Examples of other applications of the invention include fabrication of multi-layer printed circuit boards and assembly of flex circuit-to-device connections for flat-panel displays, cellular telephones, etc. Flex circuit-to-device assembly connections are typically made with an anisotropic conductive adhesive (epoxy containing a sparse distribution of conductive particles) rather than a very thin layer of non-conductive epoxy, but the need to characterize the electrical resistance of the contact between the flex circuit and the substrate (e.g., flat-panel displays) is the same.

DETAILED DESCRIPTION OF THE PREFERRED EMBODIMENTS

In a preferred embodiment of the invention, contact resistance of two conductive substrates, i.e., a flexible printed circuit in ohmic contact with a layer of electrically conductive material (e.g., metal) on the surface of a substrate (e.g., piezoelectric ceramic material) is measured. A preferred application is in the manufacture of ultrasound transducers. Most modern transducers for medical ultrasound are phased arrays, made up of single or multiple rows of electrically and mechanically independent transducer elements. One type of phased-array ultrasound transducer probe in which the invention can be incorporated comprises a transducer pallet which must be supported within a probe housing.

Figure 1:
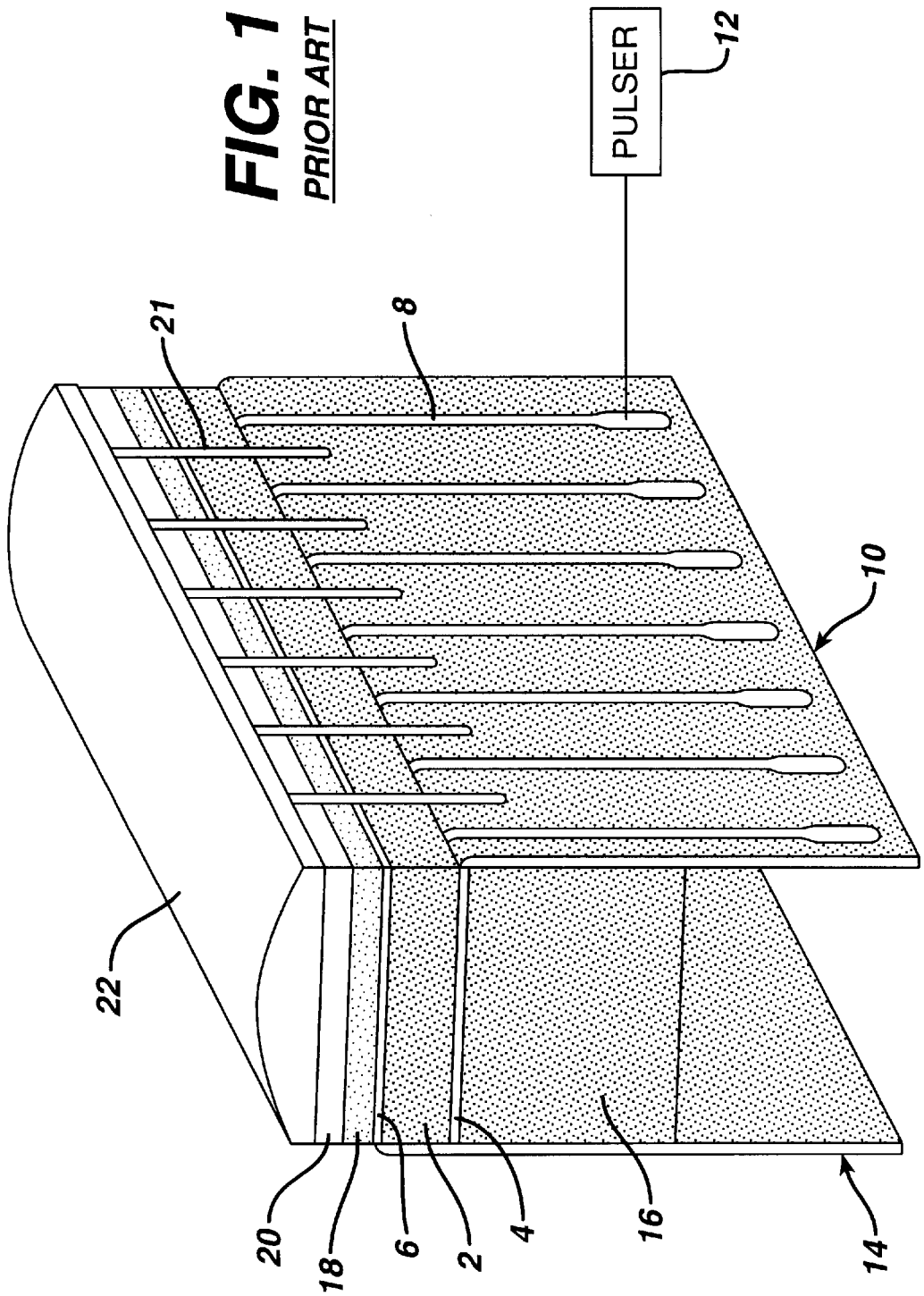
FIG. 1 is a schematic isometric view of a conventional ultrasound transducer pallet.

As shown in FIG. 1, a conventional transducer pallet comprises a linear array of narrow transducer elements. Each transducer element comprises a layer 2 of piezoelectric ceramic material. The piezoelectric material is typically lead zirconate titanate (PZT), polyvinylidene difluoride, or PZT ceramic/polymer composite. Typically, the piezoelectric ceramic material 2 of each transducer element has a signal electrode 4 formed on its rear face and a ground electrode 6 formed on its forward face. Each signal electrode 4 can be connected to a signal source, e.g., a respective pulser 12 in the transmitter (not shown) of the ultrasound imaging system to which the probe is connected via a respective conductive trace 8 on a signal flex circuit 10. The amplitude, timing and transmit sequence of the transmit pulses applied by the pulsers are controlled by the system transmitter. Each ground electrode 6 is connected to a common ground (not shown) via a respective trace (not shown) on a ground flex circuit 14. Preferably the signal and ground electrodes are connected to the respective flex circuits at the same side of the pallet (they are shown in FIG. 1 on opposite sides for illustration only). The transducer pallet also comprises a mass 16 of suitable acoustical damping material having high acoustic losses, e.g., a mixture of epoxy, silicone rubber and tungsten particles, positioned at the back surface of the transducer element array. This backing layer 16 is coupled to the rear surface of the transducer elements to absorb ultrasonic waves that emerge from the back side of each element, so that they will not be partially reflected and interfere with the ultrasonic waves propagating in the forward direction. Typically, each transducer array element also comprises a first acoustic impedance matching layer 18 bonded to the metallized forward face (which metallization forms the ground electrode) of piezoelectric ceramic layer 2. A second acoustic impedance matching layer 20 is bonded to the first acoustic impedance matching layer 18. Layers 2, 18 and 20 in the transducer pallet are bonded using acoustically transparent thin layers of adhesive. The acoustic impedance of second matching layer 20 must be less than the acoustic impedance of first matching layer 18 and greater than the acoustic impedance of the medium acoustically coupled to the transducer array.

The pallet shown in FIG. 1 has been diced into separate transducer elements, each element comprising layers 2, 4, 6, 18 and 20 laminated together to form a stack. It will be readily appreciated, however, that the undiced pallet is constructed by laminating slabs or beams to form a stack, followed by dicing the pallet to a sufficient depth to form the respective transducer elements. A dicing saw is used to form parallel element isolations cuts or kerfs 21. Each cut passes completely through acoustic matching layers 18, 20 and piezoceramic layer 2, and extends only partially into acoustic absorbing layer 16. Kerf 21 may be left empty or may be filled with a material which has a low shear modulus. After dicing, the front faces of second acoustic impedance matching layers 20 of the transducer elements are conventionally bonded to the planar rear face of a convex cylindrical lens 22 (e.g., comprised of silicone rubber) using an acoustically transparent thin layer of silicone adhesive.

Figure 2:
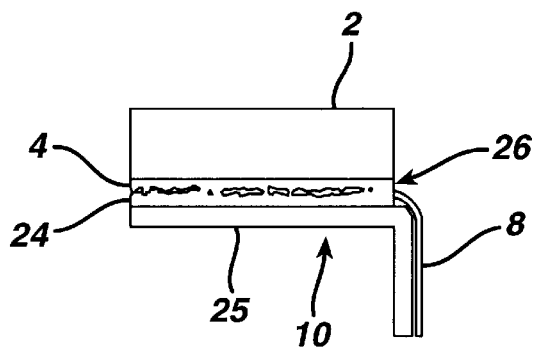
FIG. 2 is a schematic illustration showing one method of connecting a flex circuit to an electrode on a piezoceramic layer in an ultrasound transducer, in which the ohmic contact between the flex circuit and the ceramic electrode is through a non-conductive epoxy layer.

Typically, one or more flex circuits are used to make electrical connections (signal and ground) from the piezoceramic to signal processing electronics, or to a bundle of coaxial cables which ultimately connect to the signal processing electronics. One method of connecting the flex circuit(s) to the piezoceramic elements is illustrated in FIG. 2, wherein a signal electrode 4 and electrical connection to the signal flex circuit 10 are on the bottom surface of ceramic layer 2.

In particular, signal electrode 4 is electrically coupled to metallization 24 on an insulating substrate 25 of signal flex circuit 10. Although not shown in FIG. 2, it will be readily appreciated that metallization 24 may be formed on the surface of signal flex circuit 10, while conductive traces 8 of the latter may lie at a different level in the flex circuit substrate and may be electrically coupled to metallization 24 via throughholes (not shown in FIG. 2) formed in insulating substrate 25. An ohmic contact is situated between signal flex circuit 10 and signal electrode 4 through a non-conductive epoxy layer 26, represented by the white spaces between electrode 4 and metallization 24. A similar arrangement may be applied to the connection of the ground electrodes to the ground flex circuit.

In accordance with one method, metallization 24 comprises exposed metal pads formed on insulating substrate 25 of flex circuit 10. The exposed metal pads are laminated, using high pressure and a thin layer of non-conductive epoxy 26, to electrode 4 formed on the surface of piezoceramic layer 2. If the flex circuit and ceramic surfaces are microscopically rough and the epoxy layer is sufficiently thin, an electrical connection is achieved via a distribution of direct contacts between high points on the ceramic and high points on the flex circuit. The quality of such an ohmic electrical connection is very sensitive to material and process parameters which can be difficult to control. The resistances of both good and bad contacts (a few milliohms to >1 ohm) are small compared to other impedances in the circuit for a transducer element (a few tenths to about 1 ohm lead resistance in the flex circuit, in series with tens to hundreds of picoFarads from the piezoelectric), so that it is next to impossible to non-destructively measure quality of the electrical connection.

Figure 3:
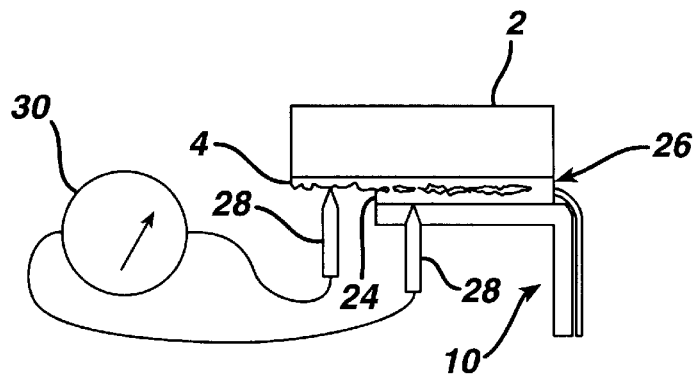
FIG. 3 is a schematic illustration showing a conventional method of measuring contact resistance between metallization on the flex circuit and the ceramic electrode shown in FIG. 2.

Typical measurements of transducer performance can detect open or severely degraded ohmic contacts but cannot discriminate between good contacts and defective or weak contacts which may degrade and become unreliable over time. If contact problems are suspected, measurement of the contact resistance requires access to the bond area. For example, as shown in FIG. 3, the back layer of the transducer pallet can be removed to obtain access to the flex circuit-to-ceramic bond area. A portion of flex circuit 10 is removed, exposing electrode 4 on piezoceramic layer 2. Probes 28 from a resistance meter 30 are respectively connected to metallization 24 on the flex circuit and to electrode 4. This method of analysis is both destructive and laborious.

Figure 4:
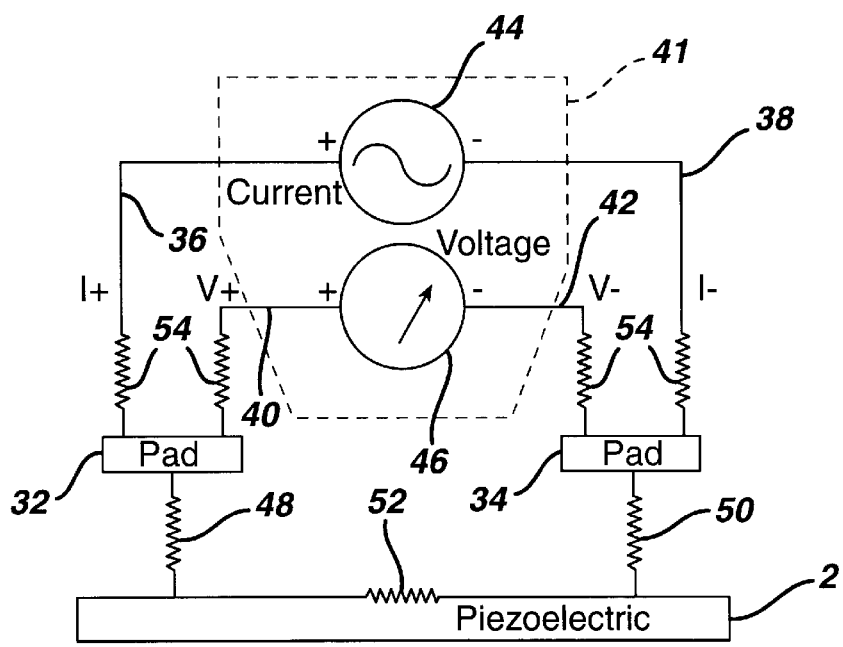
FIG. 4 is a circuit diagram of apparatus for measuring contact resistance in accordance with preferred embodiments of the invention.
Figure 6:
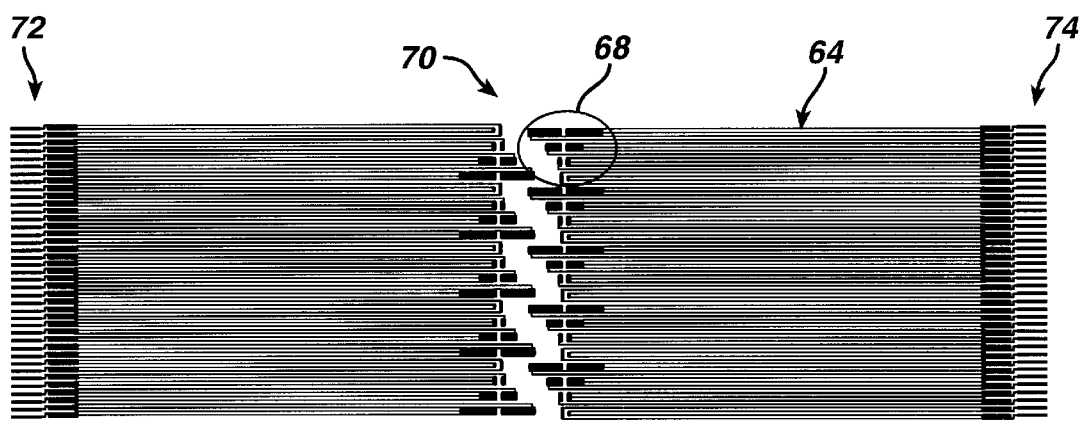
FIG. 6 is a schematic illustration showing an arrangement of leads and pads for statistical measurement of contact resistance in accordance with another preferred embodiment of the invention.
Figure 7:
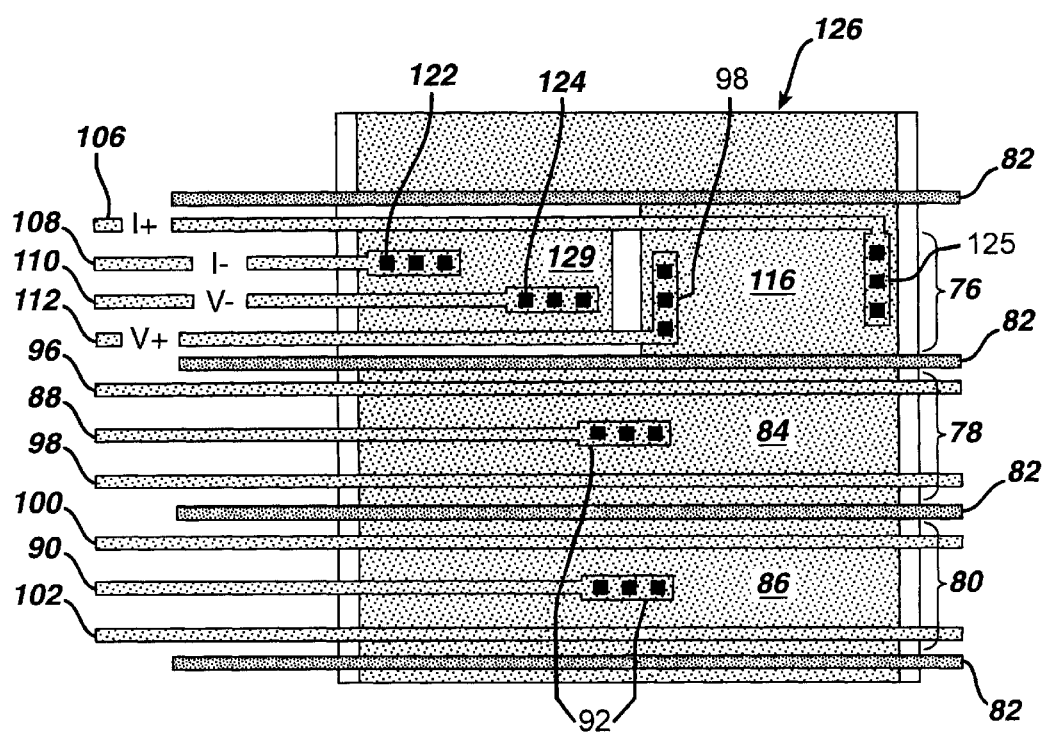
FIG. 7 is a schematic illustration of a contact resistance measurement circuit designed into an ultrasound transducer flex circuit for an ultrasound transducer array and viewed from the back of the transducer array, as though through the acoustic absorber, in accordance with yet another preferred embodiment of the invention.

A non-destructive technique for measuring the electrical properties of an ohmic contact between two materials, such as a flexible printed circuit and a metallized piezoelectric ceramic, in accordance with a preferred embodiment of the invention, is illustrated in FIG. 4. Flex circuit patterns which implement the circuit of FIG. 4 are shown in FIGS. 5–7.

The contact resistance measuring circuit shown in FIG. 4 comprises two metal pads 32 and 34 on the surface of the flex circuit, separated from each other but in close proximity thereto, and a respective pair of electrical leads from each pad to locations on the flex circuit which are accessible for probing with, e.g., a four-lead milliohmmeter 41. Electrical leads 36 and 38 respectively connect pads 32 and 34 to respective leads of a known current source 44 incorporated in the milliohmmeter, while electrical leads 40 and 42 respectively connect pads 32 and 34 to respective leads of a voltage meter 46 incorporated in the milliohmmeter. Current source 44 supplies a predetermined current, voltage meter 46 measures the resulting voltage, and the milliohmmeter computes the contact resistance based on the known current and the measured voltage. The probing locations may be remote from the flex circuit-to-metallized substrate ohmic connection. The current source, voltage meter and resistance computation circuit need not be integrally incorporated in a single unit, but may be separate units.

The resistance measured by the circuit of FIG. 4 is the sum of the two contact resistances 48 and 50 plus the resistance 52 of the electrode film between the two pads 32 and 34. Separating the current and voltage leads for a resistance measurement minimizes the effects of the lead resistances 54 and allows an accurate measurement of the resistance between the probed locations (i.e., the two pads). Locating the two pads in close proximity to each other minimizes the gap which must be bridged by the substrate electrode, and thus minimizes the contribution of the electrode sheet resistance 52 to the apparent contact resistance between the flex circuit and the substrate.

Figure 5:
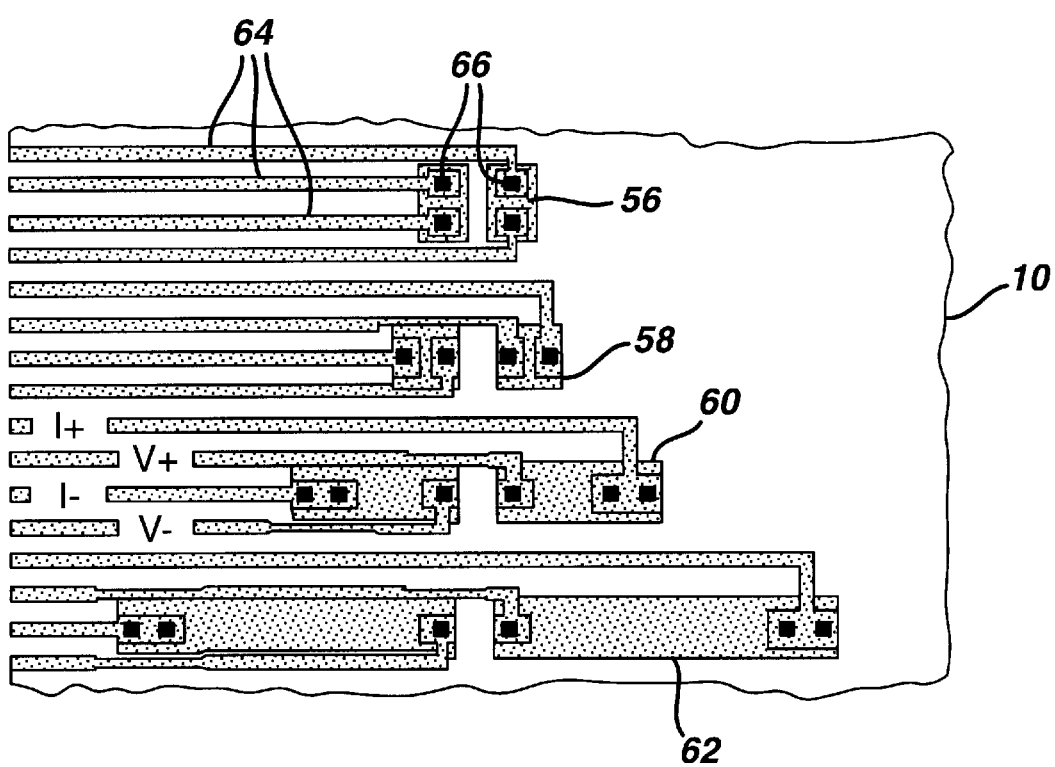
FIG. 5 is a schematic illustration showing a portion of the flex circuit supporting an arrangement of leads and pads for measuring both contact resistance and variation of resistance with contact area in accordance with a preferred embodiment of the invention.

FIG. 5 depicts an arrangement of leads and pads for measurement of contact resistance and of variation of resistance with contact area in accordance with a preferred embodiment of the invention. The squares and rectangles represent metal pads of different contact areas on the surface of flex circuit 10, which are bonded to the metallized substrate. For example, pads 56 may have a pad area of 0.1 mm×0.2 mm; pads 58 may have a pad area of 0.2 mm×0.2 mm; pads 60 may have a pad area of 0.5 mm×0.2 mm; and pads 62 may have a pad area of 1.0 mm×0.2 mm. Each pad shown in FIG. 5 is preferably connected to a pair of metal traces 64 on a different layer of the flex circuit, insulated from the metallized substrate, via through-hole connections 66. The set of four metal traces connected to a pair of metal pads may, in turn, be connected to respective leads of a four-lead milliohmmeter. The arrangement shown in FIG. 5 can be used to measure the variation of contact resistance with contact area. Since an ohmic contact depends on a random distribution of point contacts between two surfaces, both the average resistance of ohmic connections and the resistance variance should increase sharply as decreasing contact pad dimensions approach the typical distance between individual point contacts.

Accurate characterization of an ohmic connection process requires statistical measurement of a number of separate connections. FIG. 6 shows an arrangement of leads and pads for statistical measurement of contact resistance in accordance with another preferred embodiment of the invention. The circuit comprises ten identical groups. Each group 68 (one of which is indicated within an encircled region) comprises four pairs of contact pads, with relative sizes and lead connections approximately as shown in FIG. 5. Pads 70 in the center are laminated to a metallized substrate, forming ohmic contacts. All forty pairs of test pads are bonded at the same time and under identical conditions to a common substrate. Pads 72 at the left ends and pads 74 at the right ends are left exposed and used for connecting a four-lead milliohmmeter to each pair of ohmic contact pads. This allows analysis of the process capability for the ohmic connection, and the variation of that capability with pad area, with a minimum of other confounding effects.

In one experiment the contact resistance data included high four-lead resistance values and high standard deviation, which indicated a defective lamination. In this instance, lamination pressure had been too low, the epoxy bond line was too thick, and electrical connections between the flex circuit and the ceramic were consequently poor and highly variable. Resistance data from a later, well-controlled lamination showed that all connections were good and resistance variability was low. As expected, larger contact pads showed lower contact resistance and less variability. Only the smallest pads (0.02 mm$^2$) showed a standard deviation greater than ≈20% of the mean. This suggests that, for the materials and lamination process used in these experiments, contact pads larger than 0.04 mm$^2$ in area should be adequate for good ohmic contact.

FIG. 7 shows contact resistance measurement pads and leads integrated into an ultrasound transducer flex circuit in accordance with another preferred embodiment of the invention. Only three metallized ceramic element portions 76, 78 and 80 of transducer elements in a single column of a multi-row array of transducer elements are shown. Metallized ceramic elements 76, 78 and 80 are electrically and mechanically isolated by dicing cuts 82. Elements 78 and 80 form the first column in a 3 column×2 element portion of the transducer array and are bonded to respective metal pads 84 and 86 of the flex circuit. Circuit traces 88 and 90 of the flex circuit, which are respectively electrically coupled to metal pads 84 and 86 via through-hole connections 92 and 94, respectively electrically connect ceramic elements 78 and 80 to the coaxial cables of the probe. Circuit traces 96 and 98 respectively connect two elements in the second and third columns (not shown) of the first row and circuit traces 100 and 102 respectively connect two elements in the second and third columns (not shown) of the second row to the coaxial cables. The third element 76 shown in FIG. 7 is a dummy element of the transducer array. The upper four traces 106, 108, 110 and 112 are used to measure contact resistance between metal pads 114 and 116 of the flex circuit and dummy element 76 of the transducer array. Traces 106 and 112 are connected to metal pad 116 via through-hole connections 120 and 118, while traces 108 and 110 are connected to metal pad 114 via through-hole connections 122 and 124. The contact resistance for metal pads 114 and 116 and the metallized surface of dummy element 76 can be calculated by applying a known current to traces 106 and 108 and measuring the voltage between traces 110 and 112.

Figure 8:
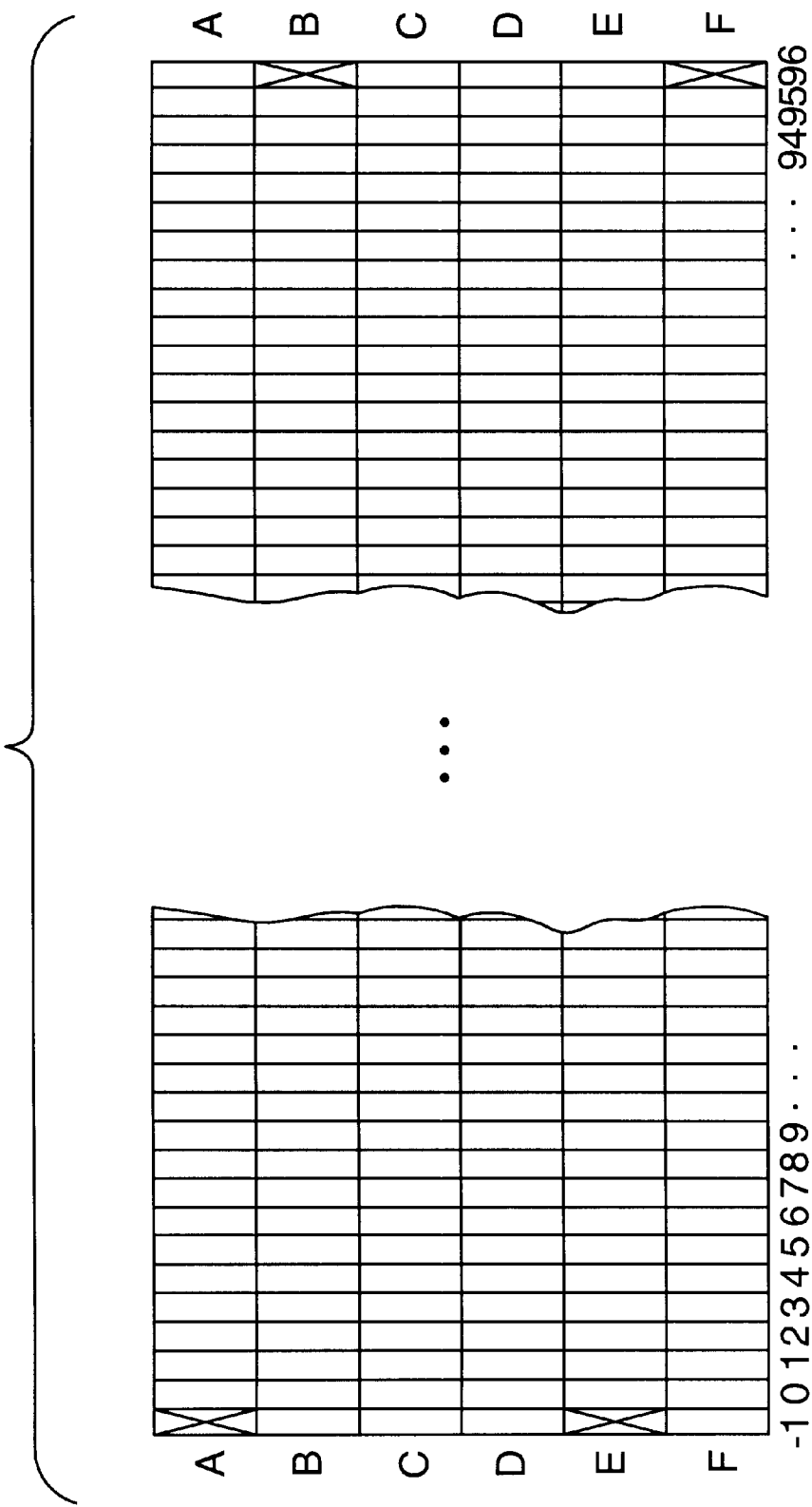
FIG. 8 is a schematic illustration depicting an ultrasound transducer array having six rows, 96 columns, and four contact measurement circuits respectively located at or near the four corners of the array.

The arrangement shown in FIG. 7 may be incorporated in a multi-row transducer at multiple locations. For example, dummy elements can be located near each of the four corners of a multi-row transducer array. In particular, the contact measurement circuits disclosed herein were incorporated in transducer arrays having six rows (A–F) and 96 columns (0–95), as schematically depicted in FIG. 8. Contact resistance measurement pads, of the type depicted in FIG. 6, were located in dummy elements (columns—1 and 96) near the four corners of the array. Specifically, two pairs of metal pads were located in the outer rows next to elements A0 and F95, to check for bond problems near the edges of the lamination stack. The other two pairs were located in inner rows next to elements B95 and E0, to check for problems in the body of the array. These dummy elements are marked with an "X" in FIG. 8. While the invention is not intended to be limited to placing contact resistance measurement pads at corners or at ends of a row, contact resistance measurement pads are preferably situated near the center and on opposite sides and/or opposite ends of a multi-row transducer array. High measured resistances on one side or on one end of the array and low measured resistances on the other side or the other end of the array would suggest that the lamination pressure had not been uniform.

It will be appreciated that FIG. 7 shows only one corner of a multi-row transducer array. Dummy element 76 is the last transducer element in a row of multiple (e.g., 96) elements. The flex circuit is preferably designed with first and second multiplicities of circuit traces starting in the center of the flex circuit and extending in opposite directions, such as shown in FIG. 6. Instead of two rows of metal contact pads, as shown in FIG. 6, if the transducer array has six rows, the flex circuit will have six rows of metal contact pads. The central region of the flex circuit is densely filled with circuit traces for signal connections between the individual transducer elements and the ultrasound imaging system. At each end of the transducer array, however, one or more dummy transducer elements are included to ensure that the first and last active elements are presented with the same mechanical boundary conditions as the elements in the middle of the array. These dummy elements are fabricated of the same materials and under the same process conditions as all other elements, and thus are ideal for measurement of contact resistance or other process parameters.

In the circuit shown in FIG. 7, one flex-to-ceramic contact pad (i.e., 116) is part of the common bus 126 which, after dicing, makes ohmic contact to an entire column of transducer elements. In particular, metal pads 84, 86 and 116 are formed from bus 126 by the dicing operation. The other contact pad (i.e., pad 114) is separate (i.e., electrically isolated) from bus 126. This feature allows the contact resistance to be measured before the piezoceramic/flex circuit laminate has been diced. After the matching layers, ceramic, flex circuit, and acoustic absorber are laminated together, a semiconductor dicing saw with a thin diamond-coated blade cuts through all of the layers to both electrically and mechanically isolate the individual transducer elements. Contact pads 114, 116 and traces 108, 110, 112, 114, which form the voltage and current measurement leads, are aligned with, and routed between, the intended paths of element isolation cuts 82.

Figure 9:
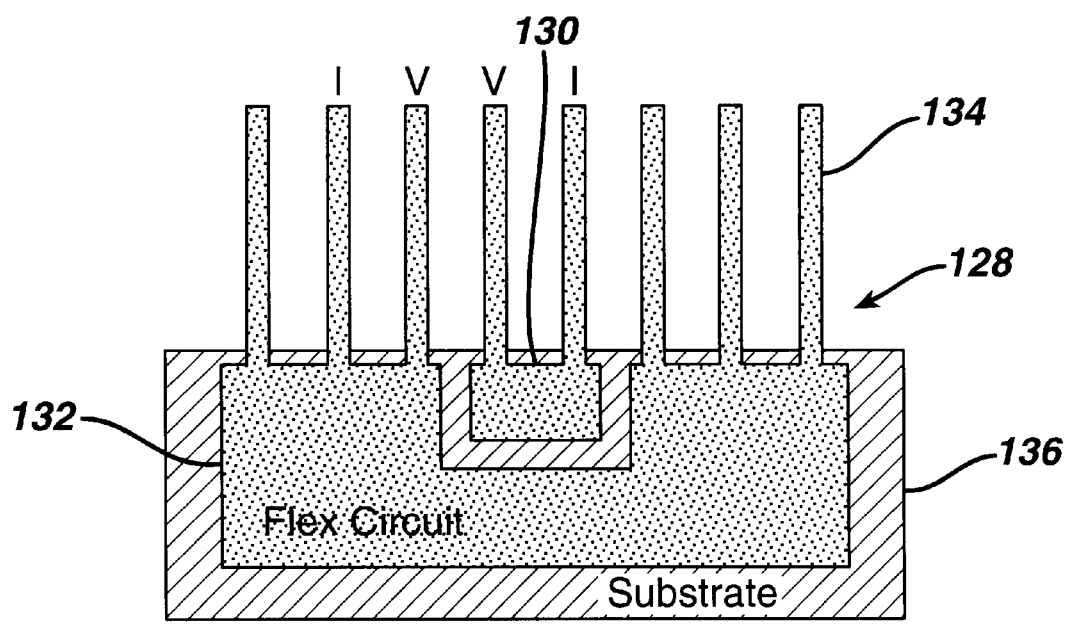
FIG. 9 is a schematic illustration of an example of a single-layer flex circuit having features for measuring contact resistance to a conductive substrate.

The preferred embodiments disclosed above have through-hole via connections, implying that the metal traces and the metal bus are on separate layers of a multi-layer flex circuit. While this is a highly versatile design of the contact resistance measurement circuit, a single-layer flex circuit may alternatively be used. A single-layer flex circuit 128 containing pads 130, 132 and traces 134 for measurement of contact resistance is shown in FIG. 9. If flex traces 134 have minimal overlap and contact with substrate 136, then flex circuit-to-substrate contact pad area is well defined and reasonable measurements of contact resistance can be made.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A system comprising an ultrasound transducer structure and a resistance meter coupled to said structure,
   wherein said structure comprises:
   a layer of piezoelectric material having a metallized surface; and
   a printed circuit comprising first and second metal pads in ohmic contact with said metallized surface of said layer of piezoelectric material and physically separated from each other, and first through fourth metal traces, said first and fourth metal traces being electrically coupled to said first metal pad, and said second and third metal traces being electrically coupled to said second metal pad; and
   wherein said resistance meter is electrically coupled to said first through fourth metal traces in such manner that said resistance meter provides a direct resistance measurement of said ohmic contact.

2. A method of measuring contact resistance between a printed circuit board and a metallized face of diced piezoceramic material in an ultrasound transducer array, comprising the steps of:
   forming first and second metal pads and first through fourth metal traces on said printed circuit board, said first and second metal pads being physically separated from each other, said first metal pad being electrically coupled to said first and fourth metal traces, and said second metal pad being electrically coupled to said second and third metal traces;
   bonding said first and second metal pads to said metallized face using a thin layer of bonding material;
   electrically coupling first and second leads of a current source to said first and second metal pads respectively;
   electrically coupling first and second leads of a voltage meter to said first and second metal pads respectively; and
   determining said contact resistance based on current supplied by said current source and resulting voltage measured by said voltage meter.

3. An ultrasound system, comprising:
   an ultrasound transducer array comprising a row of N transducer elements, each of said N transducer elements comprising a layer of piezoelectric material having a metallized surface;
   a printed circuit board comprising a substrate of electrically insulating material and N+1 metal pads supported by said insulating substrate and physically separated from each other, the first and second of said N+1 metal pads being in ohmic contact with the metallized surface of the first of said N transducer elements, and each of the third through (N+1)-th metal pads being in ohmic contact with the metallized surface of a respective one of said second through N-th transducer elements;
   bonding material for bonding said printed circuit board to said N transducer elements; and
   a resistance meter electrically coupled to said N+1 metal pads for providing a direct resistance measurement of said ohmic contacts.

* * * * *